(12) United States Patent
Borschke

(10) Patent No.: US 9,937,168 B2
(45) Date of Patent: Apr. 10, 2018

(54) NICOTINE-CONTAINING PHARMACEUTICAL COMPOSITIONS

(71) Applicant: NICONOVUM USA, INC., Winston-Salem, NC (US)

(72) Inventor: August J. Borschke, Winston-Salem, NC (US)

(73) Assignee: Niconovum USA, Inc., Winston-Salem, NC (US)

( * ) Notice: Subject to any disclaimer, the term of this patent is extended or adjusted under 35 U.S.C. 154(b) by 0 days.

(21) Appl. No.: 15/617,849

(22) Filed: Jun. 8, 2017

(65) Prior Publication Data

US 2017/0326138 A1    Nov. 16, 2017

Related U.S. Application Data

(62) Division of application No. 12/775,910, filed on May 7, 2010.

(51) Int. Cl.
| | | |
|---|---|---|
| A61K 31/498 | (2006.01) | |
| A61K 31/465 | (2006.01) | |
| A61K 9/20 | (2006.01) | |
| A61K 9/16 | (2006.01) | |
| A61K 9/68 | (2006.01) | |
| A61K 9/00 | (2006.01) | |
| A61K 9/12 | (2006.01) | |

(52) U.S. Cl.
CPC ........... *A61K 31/498* (2013.01); *A61K 9/009* (2013.01); *A61K 9/0053* (2013.01); *A61K 9/0058* (2013.01); *A61K 9/12* (2013.01); *A61K 9/1652* (2013.01); *A61K 9/20* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 3,877,468 A | 4/1975 | Lichtneckert et al. | |
| 5,593,684 A | 1/1997 | Baker et al. | |
| 5,741,802 A | 4/1998 | Kem et al. | |
| 6,248,760 B1 | 6/2001 | Wilhelmsen | |
| 6,344,222 B1 | 2/2002 | Cherukuri et al. | |
| 6,676,959 B1 | 1/2004 | Andersson et al. | |
| 6,893,654 B2 | 5/2005 | Pinney et al. | |
| 7,714,001 B2 * | 5/2010 | Schmitt ................ | A61K 31/506 514/343 |
| 2004/0191322 A1 | 9/2004 | Hansson | |
| 2007/0163610 A1 | 7/2007 | Lindell et al. | |
| 2009/0004249 A1 | 1/2009 | Gonda | |
| 2009/0023819 A1 | 1/2009 | Axelsson | |
| 2009/0092573 A1 | 4/2009 | Andersen | |
| 2009/0293895 A1 | 12/2009 | Axelsson et al. | |
| 2010/0004294 A1 | 1/2010 | Axelsson et al. | |
| 2010/0004451 A1 | 1/2010 | Ahmad et al. | |
| 2010/0040679 A1 | 2/2010 | Chang et al. | |
| 2010/0061940 A1 | 3/2010 | Axelsson et al. | |

FOREIGN PATENT DOCUMENTS

| | | | |
|---|---|---|---|
| EP | 1 458 388 B1 | 4/2009 | |
| WO | WO 2002/076211 A1 | 10/2002 | |
| WO | WO 2003/070731 A2 | 8/2003 | |
| WO | WO 2004/076449 A2 | 9/2004 | |
| WO | WO 2006/069097 A2 | 6/2006 | |
| WO | WO 2006/100075 A2 | 9/2006 | |
| WO | WO 2007/104575 A2 | 9/2007 | |
| WO | WO 2008/037470 A1 | 4/2008 | |
| WO | WO 2009/080021 A1 | 7/2009 | |
| WO | WO-2009080021 A1 * | 7/2009 | ............. A23G 4/043 |

OTHER PUBLICATIONS

Ebbert, Jon O. et al., "Combination Treatment with Varenicline and Nicotine Replacement Therapy," *Nicotine & Tobacco Research*, vol. 11, No. 5, (2009) pp. 572-576.
Ebbed, Jon O. et al., "Combination Pharmacotherapy for Stopping Smoking: What Advantages Does It Offer," *Drugs*, (2011) pp. 1-10.
Zierler-Brown, S. et al., "Oral Varenicline for Smoking Cessation," *The Annals of Pharmacotherapy*, (2007) vol. 41, pp. 95-99.
Arneric, Stephen P., et al., "Neuronal Nicotinic Receptors: A Perspective on Two Decades of Drug Discovery Research," Biochemical Pharmacology, vol. 74, (2007) pp. 1092-1101.
Biton, Bruno, et al., "SSR 180711, a Novel Selective α7 Nicotinic Receptor Partial Agonist: (I) Binding and Functional Profile," Neuropsychopharmacology, vol. 32, (2007), pp. 1-16.
Cohen, C., et al., "The Selective α4β2 Nicotinic Receptor Partial Agonist, SSR591813, Reduces Nicotine Dependence in Rats," Society for Neuroscience, Pres. No. 811.5 (2002), Abstract. http://www.sfn.org/index.cfm?pagename=abstracts_archive&task=view&controlID=12189 . . . Sep. 10, 2010.
Dunbar, G., et al., "Effects of TC-1734 (AZD3480), a Selective Neuronal Nicotinic Receptor Agonist, on Cognitive Performance and the EEG of Young Healthy Male Volunteers," Psychopharmacology, vol. 191 (2007), pp. 919-929.
Dwoskin, Linda P. et al., "Recent Developments in Neuronal Nicotinic Acetylcholine Receptor Antagonists," Expert Opinion on Therapeutic Patents, vol. 10:10, (2000), pp. 1561-1581.
Fagerstrom, Karl Olov, "Combined Use of Nicotine Replacement Products," Health Values, vol. 18 (1994), pp. 15-20.

(Continued)

*Primary Examiner* — Johann R Richter
*Assistant Examiner* — Courtney A Brown
(74) *Attorney, Agent, or Firm* — Brinks Gilson & Lione

(57) ABSTRACT

A composition intended to be employed for therapeutic purposes incorporates nicotine and at least one other nicotinic compound. Representative forms of nicotine can be as a free base (e.g., as a mixture of nicotine and microcrystalline cellulose), as a form of nicotine salt (e.g., as nicotine bitartrate) or as nicotine polacrilex. The other nicotinic compound is a compound that can be considered to bind selectively to certain nicotinic receptor subtypes, and particularly those of the central nervous system. For example, the other nicotinic compound can be a compound that binds selectively to the nicotinic receptor subtypes $\alpha_7$ or $\alpha_4\beta_2$. The composition is useful for treatment of central nervous system conditions, diseases and disorders, and as a nicotine replacement therapy.

18 Claims, No Drawings

(56) References Cited

OTHER PUBLICATIONS

Hajós, M., et al., "*The Selective α7 Nicotinic Acetylcholine Receptor Agonist PNU-282987 [N-[(3R)-1-Azabicyclo [2.2.2] oct-3-yl]-4-chlorobenzamide Hydrochloride] Enhances GABAergic Synaptic Activity in Brain Slices and Restores Auditory Gating Deficits in Anesthetized Rats*," Journal of Pharmacology and Experimental Therapeutics, vol. 312, No. 3 (2005), pp. 1213-1222.

Harrington, Kathleen F., et al., "*Smoking Cessation Through the Utilization of Pharmacotherapy*," Expert Reviews Resp. Med, vol. 3:5, (2009), pp. 475-485.

Hauser, T.A., et al., "*TC-5619: An Alpha7 Neuronal Nicotinic Receptor-Selective Agonist That Demonstrates Efficacy in Animal Models of the Positive and Negative Symptoms and Cognitive Dysfunction of Schizophrenia*," Biochemical Pharmacology, vol. 78, (2009), pp. 803-812.

Huang, Xiaoqin, et al., "*Modeling Multiple Species of Nicotine and Deschloroepibatidine Interacting with α4β2 Nicotinic Acetylcholine Receptor: From Microscopic Binding to Phenomenological Binding Affinity*," Journal of American Chemical Society, vol. 127, (2005), pp. 14401-14414.

Jorenby, Douglas E., et al., "*Efficacy of Varenicline, an α4β2 Nicotinic Acetylcholine Receptor Partial Agonist, vs Placebo or Sustained-Release Bupropion for Smoking Cessation*," JAMA, vol. 296, No. 1 (2006), pp. 56-63.

Laniado-Laborin, Rafael, "*Smoking Cessation Intervention: An Evidence-Based Approach*,", Postgraduate Medicine, vol. 122, Issue 2, (2010), pp. 74-82.

Li, Jian-Guo, et al., "*Nicotinic Acetylcholine Receptors and Modulation of Learning in 4- and 27-Month-Old Rabbits*," Neuropsycopharmacology, vol. 33, (2008), pp. 2820-2830.

Lockhart, B.P., et al., "*Pharmacological Evaluation of Two Novel Centrally Acting Nicotinic Acetylcholine Receptor Compounds*," Society for Neuroscience Abstract, Pres. No. 684.9, (2002). http://www.sfn.org/index.cfm?pagename=abstracts_archive&task=view&controlID=10334 . . . Sep. 24, 2010.

Malysz, John, et al., "*Evaluation of α7 Nicotinic Acetylcholine Receptor Agonists and Positive Allosteric Modulators Using the Parallel Oocyte Electrophysiology Test Station*," Assay Drug Development Technologies, (2009), pp. 374-390.

Millar, Neil S., "*A Review of Experimental Techniques Used for the Heterologous Expression of Nicotinic Acetylcholine Receptors*," Biochemical Pharmacology, vol. 78, (2009), pp. 766-776.

Rollema, Hans, et al., "*Varenicline Has Antidepressant-Like Activity in the Forced Swim Test and Augments Sertraline's Effect*," European Journal of Pharmacology vol. 605(1-3); (2009), pp. 114-116.

Roncarati, Renza, et al., "*Procognitive and Neuroprotective Activity of a Novel α7 Nicotinic Acetylcholine Receptor Agonist for Treatment of Neurodegenerative and Cognitive Disorders*," Journal of Pharmacology and Experimental Therapeutics, vol. 329, (2009), pp. 459-468.

Schmitt, Jeffrey D., et al., "*Chapter 5. Targeting Nicotinic Acetylcholine Receptors: Advances in Molecular Design and Therapies*," Annual Reports in Medical Chemistry, vol. 35 (2000), pp. 41-51.

Schreiber, Rudy, et al., "*Effects of $α_4/β_2$- and $α_7$-Nicotine Acetylcholine Receptor Agonists on Prepulse Inhibition of the Acoustic Startle Response in Rats and Mice*," Psychopharmacology, vol. 159 (2002), pp. 248-257.

Siok, C.J., et al., "*Short Communication Activation of α7 Acetylcholine Receptors Augments Stimulation-Induced Hippocampal Theta Oscillation*," European Journal of Neuroscience, vol. 23 (2006), pp. 570-574.

Thomsen, M.S., et al., "*The Selective α7 Nicotinic Acetylcholine Receptor Agonist A-582941 Activates immediate Early Genes in Limbic Regions of the Forebrain: Differential Effects in the Juvenile and Adult Rat*,"Neuroscience, vol. 154, (2008), pp. 741-753.

Zierler-Brown, Seena L. et al., "*Oral Varenicline for Smoking Cessation*," The Annals of Pharmacotherapy, vol. 41 (2007), pp. 95-99.

Zhu, Chang Z., et al., "*In vivo characterization of the co-Administration of α4β2 Neuronal Nicotinic Receptor Agonist and Positive Allosteric Modulator in Experimental Pain in Rats*," Biochemical Pharmacology, vol. 78 (2009), pp. 899-925.

PCT Search Report corresponding to PCT Application No. PCT/US2011/034240 (WO2011/139811), dated Jul. 27, 2011, 3p.

\* cited by examiner

NICOTINE-CONTAINING PHARMACEUTICAL COMPOSITIONS

This application is a divisional of U.S. patent application Ser. No. 12/775,910, filed May 7, 2010, the entirety of which is hereby incorporated by reference.

FIELD OF THE INVENTION

The present invention relates to compositions that contain nicotine, and in particular, to nicotine-containing pharmaceutical compositions intended to be administered to provide a pharmacological effect, or otherwise used for therapeutic purposes.

BACKGROUND

Central nervous system (CNS) conditions, diseases, or disorders can be drug induced; can be attributed to genetic predisposition, infection or trauma; or can be of unknown etiology. They comprise neuropsychiatric disorders, neurological diseases and mental illnesses; and include neurodegenerative diseases, behavioral disorders, cognitive disorders and cognitive affective disorders. The clinical manifestations of several CNS conditions, diseases or disorders have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors).

Nicotinic compounds, such as nicotine, are capable of affecting nicotinic acetylcholinergic receptors (nAChRs). Subtypes of nAChRs exist in both the CNS and the peripheral nervous system (PNS), but the distribution of subtypes is heterogeneous. For instance, certain subtypes which are predominant in vertebrate brain, others predominate at the autonomic ganglia, and others predominate at neuromuscular junction. Activation of nAChRs by nicotinic compounds results in neurotransmitter release. See, for example, Dwoskin et al., *Exp. Opin. Ther. Patents*, 10: 1561-1581 (2000); Schmitt et al., *Annual Reports in Med. Chem.*, 35: 41-51 (2000); Huang et al., *J. Am. Chem. Soc.*, 127: 14401-14414 (2006); Arneric et al., *Biochem. Pharmacol.*, 74: 1092-1101 (2007) and Millar, *Biochem. Pharmacol.*, 78: 766-776 (2009), which are incorporated herein by reference.

It has been suggested that administration of nicotine, and other nicotinic compounds, can result in various pharmacological effects. See, for example, U.S. Pat. No. 5,583,140 to Bencherif et al.; U.S. Pat. No. 5,723,477 to McDonald et al.; U.S. Pat. No. 7,001,900 to Jacobsen et al.; U.S. Pat. No. 7,135,484 to Dart et al. and U.S. Pat. No. 7,214,686 to Bencherif et al.; and US Pat. Pub. No. 2010/0004451 to Ahmad et al., which are incorporated herein by reference. As a result, it has been suggested that nicotine, and other nicotinic compounds, can exhibit utility in the treatment of a wide variety of conditions, diseases, and disorders, including those that affect the CNS. Additionally, administration of nicotine and nicotinic compounds has been proposed for treatment of certain other conditions, diseases, and disorders. See, for example, U.S. Pat. No. 5,604,231 to Smith et al.; U.S. Pat. No. 5,811,442 to Bencherif et al.; U.S. Pat. No. 6,238,689 to Rhodes et al.; and U.S. Pat. No. 6,489,349 to Bencherif et al., which are incorporated herein by reference. Furthermore, administration of nicotine has been employed in an effort to help cigarette smokers quit smoking (i.e., as a smoking cessation aid). For example, nicotine has been an active ingredient of various types of so-called "nicotine replacement therapy" or "NRT" products.

It has been proposed to administer nicotine using a transdermal patch. Representative types of nicotine-containing transdermal patch products have been marketed under the tradenames "Habitrol," "Nicoderm," "Nicorette," "Nicorette CQ," "NicotineII" and "ProStep." See also, for example, U.S. Pat. No. 4,597,961 to Etscom; U.S. Pat. No. 5,298,257 to Bannon et al.; U.S. Pat. No. 5,603,947 to Wong et al.; U.S. Pat. No. 5,834,011 to Rose et al.; U.S. Pat. No. 6,165,497 to Osborne et al.; and U.S. Pat. No. 6,676,959 to Anderson et al., which are incorporated herein by reference. It also has been suggested that transdermal administration of nicotine can be accompanied by ingestion of other types of nicotine-containing products. See, for example, U.S. Pat. No. 5,593,684 to Baker et al.; US Pat. Pub. No. 2009/0004249 to Gonda; and Fagerstrom, *Health Values*, 18:15 (1994), which are incorporated herein by reference.

One particularly popular way to provide for oral administration of nicotine has been through the use of nicotine-containing gum. Nicotine-containing gum products have been marketed under the tradenames "Nicorette," "NicotineII" and "Zonnic." See also, for example, U.S. Pat. No. 3,845,217 to Ferno et al.; U.S. Pat. No. 3,877,468 to Lichtneckert et al.; U.S. Pat. No. 3,901,248 to Lichtneckert et al.; U.S. Pat. No. 6,344,222 to Cherukuri et al.; U.S. Pat. No. 6,358,060 to Pinney et al.; U.S. Pat. No. 6,773,716 to Ream et al.; and U.S. Pat. No. 6,893,654 to Pinney et al.; and US Pat. Pub. No. 2004/0191322 to Hansson, which are incorporated herein by reference.

Another way that has been employed to provide oral administration of nicotine has been through the use of nicotine-containing lozenge or tablet types of products. Nicotine-containing lozenge, mini lozenge, tablet, and microtab types of products have been marketed under the tradenames "Commit," "Nicorette," "NicotineII" and "NiQuitin." See also, for example, U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; and U.S. Pat. No. 6,248,760 to Wilhelmsen; US Pat. Pub. No. 2001/0016593 to Wilhelmsen and No. 2010/0004294 to Axelsson et al., which are incorporated herein by reference.

Nicotine also has been administered in the form of nasal or oral sprays. Various exemplary ways to administer nicotine in the form of a nasal spray are set forth in U.S. Pat. No. 4,579,858 to Ferno et al.; U.S. Pat. No. 5,656,255 to Jones; and U.S. Pat. No. 6,596,740 to Jones; which are incorporated herein by reference. Various exemplary ways to administer nicotine in the form of an oral spray, such as for buccal administration, are set forth in U.S. Pat. No. 6,024,097 to Von Wielligh; US Pat. Pub. No. 2003/0159702 to Lindell et al.; No. 2007/0163610 to Lindell et al. and No. 2009/0023819 to Axelsson; EP 1458388 to Lindell et al.; and PCT WO 2008/037470 to Axelsson et al., which are incorporated herein by reference. Nicotine-containing sprays have been marketed under the tradenames "Nicotrol NS," "Quit" and "Zonnic."

Various other ways to administer nicotine for the purpose of providing a therapeutic effect have been proposed. For example, it has been suggested that nicotine can be incorporated into orally dissolving films (e.g., U.S. Pat. No. 6,709,671 to Zerbe et al.; U.S. Pat. No. 7,025,983 to Leung et al.; and U.S. Pat. No. 7,491,406 to Leung et al.; and US Pat. Pub. No. 2006/0198873 to Chan et al. and No. 2006/0204559 to Bess et al.); oral osmotic devices (e.g., U.S. Pat. No. 5,147,654 to Place et al.); gum pads (e.g., U.S. Pat. No.

6,319,510 to Yates); oral patches (e.g., US Pat. Pub. No. 2006/0240087 to Houze et al.); snuff-type forms in pouches or sachets (e.g., U.S. Pat. No. 4,907,605 to Ray et al. and US Pat. Pub. No. 2009/0293895 to Axelsson et al.); lip balm (e.g., U.S. Pat. No. 7,105,173 to Rolling) and beverages (e.g., U.S. Pat. No. 6,268,386 to Thompson; U.S. Pat. No. 7,115,297 to Stillman; and U.S. Pat. No. 7,435,749 to Knight). It also has been suggested that nicotine can be delivered using various types of inhalation devices and vapor delivery systems (e.g., U.S. Pat. No. 4,284,809 to Ray; U.S. Pat. No. 4,800,903 to Ray et al.; U.S. Pat. No. 6,234,169 to Bulbrook et al.; U.S. Pat. No. 6,874,507 to Farr; and US Pat. Pub. No. 2006/0018840 to Lechuga-Ballesteros and No. 2009/0005423 to Gonda; and EP 1,618,803 to Hon).

It would be desirable to provide a composition capable of delivering or administering nicotine for therapeutic purposes.

BRIEF SUMMARY

In one aspect, the present invention relates to a composition intended to be employed for therapeutic purposes. The composition includes a form that is pharmaceutically effective or pharmaceutically acceptable. The composition incorporates a nicotinic compound that is considered to be non-selective (i.e., is not considered to discriminate) among the various nAChRs in the CNS and PNS. An example of such a compound is nicotine. The composition incorporates at least one other nicotinic compound. The other nicotinic compound is a compound that exhibits selectivity to nicotinic receptor subtypes within the CNS. Other nicotinic compounds that are highly preferred act as agonists, and representative agonists are selective to nAChRs such as $\alpha_7$ and $\alpha_4\beta_2$. The nicotine can be as a free base (e.g., as a mixture of nicotine and microcrystalline cellulose), as another form of nicotine salt (e.g., as nicotine bitartrate) or as nicotine polacrilex. In a highly preferred embodiment, the composition that incorporates at least two nicotinic active ingredients is provided in a single dosage form or unit, which is intended to be administered by oral means.

In another aspect, the present invention relates to a method for providing treatment for a condition, disease or disorder. The method involves administering to a human subject, such as a subject in need thereof, an effective amount of a composition incorporating a nicotinic compound that is considered to be non-selective among the various nAChRs in the CNS and PNS (e.g., nicotine) and at least one other nicotinic compound. The other nicotinic compound is a compound that exhibits selectivity to nAChRs within the CNS. Other nicotinic compounds that are highly preferred act as agonists, and are selective to nAChRs such as $\alpha_7$ and $\alpha_4\beta_2$. In a highly preferred embodiment, the composition is administered by oral means.

Compositions of the present invention, including compositions incorporating other pharmaceutically acceptable excipient ingredients, can be provided in forms suitable for administration to human subjects. Exemplary formats and configurations for oral administration of nicotine-containing compositions for therapeutic purposes include gum, tablet, lozenge, pouch and mouth-spray types of products.

Compositions of the present invention can be used to treat a wide variety of diseases, conditions and disorders, particularly those of the CNS. Additionally, those compositions can be used as smoking cessation aids (e.g., as components of NRT).

DETAILED DESCRIPTION OF THE DRAWINGS AND THE PRESENTLY PREFERRED EMBODIMENTS

The present inventions now will be described more fully hereinafter. The invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise.

Embodiments of the present invention include the use of nicotinic compounds for therapeutic purposes and provide compositions adapted for oral or nasal delivery of nicotinic compounds. As used herein, "nicotinic compound" refers to a compound capable of affecting a nicotinic acetylcholinergic receptor (nAChR). Preferably, a nicotinic compound is an agonist of a nicotinic acetylcholinergic receptor. As used herein, "agonist" refers to a compound that binds to a receptor and triggers a response. The term "agonist" includes full agonists, partial agonists and superagonists. Full agonists bind to the receptor and mimic the response produced by binding of the natural ligand for the receptor. Partial agonists bind the receptor and produce a response, but are less efficacious in producing the response as compared to the natural ligand for the receptor. Superagonists bind the receptor and produce a response, but are more efficacious in producing the response as compared to the natural ligand for the receptor. As used herein, a "source of nicotine" refers to naturally-occurring or synthetic nicotine unbound from a plant material, meaning the compound is at least partially purified and not contained within a plant structure such as a tobacco leaf. Most preferably, nicotine is naturally-occurring and obtained as an extract from a *Nicotiana* species (e.g., tobacco). The nicotine may include the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine) or an enantiomerically enriched mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis. Despite the fact that nicotine can be extracted from *Nicotiana* species, it is highly preferred that the nicotine (and the composition and products produced in accordance with the present invention) are virtually or essentially absent of other components obtained from or derived from tobacco.

The source of nicotine of the nicotine-containing compositions of the invention can include nicotine in free base form, salt form, as a complex, as a solvate, or other suitable form. See, for example, the discussion of nicotine in free base form in US Pat. Pub. No. 2004/0191322 to Hansson, which is incorporated herein by reference. At least a portion of the nicotinic compound can be employed in the form of a resin complex of nicotine where nicotine is bound in an ion exchange resin such as nicotine polacrilex. See, for example, U.S. Pat. No. 3,901,248 to Lichtneckert et al.; which is incorporated herein by reference. At least a portion of the nicotine can be employed in the form of a salt. Salts of nicotine can be provided using the types of ingredients and techniques set forth in U.S. Pat. No. 2,033,909 to Cox et al.

and Perfetti, Beitrage Tabakforschung Int., 12: 43-54 (1983), which are incorporated herein by reference. Additionally, salts of nicotine have been available from sources such as Pfaltz and Bauer, Inc. and K&K Laboratories, Division of ICN Biochemicals, Inc. Furthermore, combinations of forms of nicotine, or combinations of nicotine salts, can be employed. See, for example, U.S. patent application Ser. No. 12/769,335, filed Apr. 28, 2010, to Brinkley et al.; which is incorporated herein by reference.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein.

When nicotinic compounds of the present invention contain relatively basic functionalities, as in nicotine, for example, acid addition salts can be obtained by contacting the neutral form of such compounds with a sufficient amount of the desired acid, either neat or in a suitable inert solvent. Exemplary pharmaceutically acceptable nicotine salts include tartrate (e.g., nicotine tartrate and nicotine bitartrate), chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. One skilled in the art will appreciate that analogous salts can be formed for agonist compounds comprising relatively basic functionalities. Additional acids that can form salts include formic, acetic, propionic, isobutyric, butyric, alpha-methylbutyric, isovaleric, levulinic, beta-methylvaleric, caproic, 2-furoic, benzoic, phenylacetic, heptanoic, octanoic, nonanoic, oxalic, malonic, glycolic acid, benzenesulfonic, camphosulfonic, ethanesulfonic, gluconic, glucoronic, glutamic, hippuric, hydrobromic, isethionic, lactobionic, maleic, mandelic, methanesulfonic, mucic, naphthalenesulfonic, nicotinic, nitric, pamoic, pantothenic, phosphoric, sulfuric and the like as well as other fatty acids having carbon chains of up to about 20 carbon atoms.

Although nicotinic compounds of the present invention may include relatively acidic functionalities less frequently, base addition salts may be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts may also be derived from pharmaceutically-acceptable organic bases including salts of primary, secondary, tertiary and quaternary amines.

Also included are salts of amino acids such as arginate and the like, and salts of organic acids like glucuronic or galactunoric acids and the like (see, for example, Berge, S. M. et al, "Pharmaceutical Salts", *J. Pharmaceutical Science*, 1977, 66:1-19). Certain compounds may contain both basic and acidic functionalities that allow the compounds to be converted into either base or acid addition salts.

In addition to salt forms, also included are compounds which are in a pro-drug form. Pro-drugs of the compounds described herein are those compounds that readily undergo chemical changes under physiological conditions to provide the compounds of the present invention. Additionally, pro-drugs can be converted to the compounds of the present invention by chemical or biochemical methods in an ex vivo environment. For example, pro-drugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and may be used within the scope of the present invention.

The composition preferably includes another nicotinic compound other than nicotine, and most preferably, that nicotinic compound can be characterized as a selective agonist to nicotinic receptor subtypes that are present in the brain, or that can otherwise be characterized as a compound that modulates nicotinic receptor subtypes of the CNS. Various nicotinic receptor subtypes are described in Dwoskin et al., *Exp. Opin. Ther. Patents*, 10: 1561-1581 (2000); Huang et al., *J. Am. Chem. Soc.*, 127: 14401-14414 (2006) and Millar, *Biochem. Pharmacol.*, 78: 766-776 (2009); which are incorporated herein by reference. Representative compounds that can be characterized as other nicotinic compounds for purposes of this invention are set forth in Schmitt et al., *Annual Reports in Med. Chem.* 35: 41-51 (2000) and Arneric et al., *Biochem. Pharmacol.*, 74: 1092-1101 (2007); which are incorporated herein by reference.

In one aspect, the other nicotinic compound can be a compound has selectivity to the $\alpha_7$ (alpha 7) nicotinic receptor subtype, and preferably is an agonist of the $\alpha_7$ nicotinic receptor subtype. Several compounds having such $\alpha_7$ receptor subtype selectivity have been reported in the literature. For example, various compounds purported to have selectivity to the $\alpha_7$ nicotinic receptor subtype are set forth in Malysz et al., *Assay Drug Dev. Tech.*, August: 374-390 (2009). An example of one such nicotinic compound is N-[(2S,3S)-2-(pyridin-3-ylmethyl)-1-azabicyclo[2.2.2]oct-3-yl]-1-benzofuran-2-carboxamide (also known as TC-5619). See, for example, Hauser et al., *Biochem. Pharmacol.*, 78: 803-812 (2009). Another representative is compound is (5aS,8S,10aR)-5a,6,9,10-Tetrahydro,7H,11H-8,10a-methanopyrido [2',3':5,6]pyrano[2,3-d]azepine (also known as dianicline or SSR591813 or SSR-591,813). See, for example, Hajos et al., *J. Pharmacol. Exp. Ther.*, 312: 1213-1222 (2005). Another representative compound is 1,4-Diazabicyclo[3.2.2]nonane-4-carboxylic acid, 4-bromophenyl ester (also known as SSR180711). See, for example, Biton et al., *Neuropsychopharmacol.*, 32: 1-16 (2007). Another representative compound is 3-[(3E)-3-[(2,4-dimethoxyphenyl)methylidene]-5,6-dihydro-4H-pyridin-2-yl]pyridine (also known as GTS-21). See, for example, U.S. Pat. No. 5,516,802 to Zoltewicz et al. and U.S. Pat. No. 5,741,802 to Kem et al. Another representative compound is 2-methyl-5-(6-phenyl-pyridazin-3-yl)-octahydro-pyrrolo[3,4-c]pyrrole (also known as A-582941). See, for example, Thomsen et al., *Neuroscience*, 154: 741-753 (2008). Another representative compound is (5S)-spiro[1,3-oxazolidine-5,8'-1-azabicyclo[2.2.2]octane]-2-one (also known as AR-R-17779 or AR-R-17779). See, for example, Li et al., *Neuropsycopharmacol.*, 33: 2820-2830 (2008). Another representative compound is N-[(3R)-1-azabicyclo[2.2.2]oct-3-yl]-4-chlorobenzamide (also known as PNU-282,987). See, for example, Siok et al., *Eur. J. Neurosci.*, 23: 570-574

(2006). Another representative compound is 5-morpholin-4-yl-pentanoic acid (4-pyridin-3-yl-phenyl)-amide (also known as WAY-317,538 or SEN-12333). See, for example, Roncarati et al., *J. Pharmacol. Exp. Ther.*, 329: 459-468 (2009). Yet other examples are compounds are those designated as EVP-6124 and EVP-4473 by Envivo Pharmaceuticals, Inc., TC-6987 by Targacept, Inc. and MEM3454 by Memory Pharmaceuticals Corp. The foregoing cited references are incorporated herein by reference.

In one aspect, the nicotinic compound other than nicotine can be a compound that has selectivity to the $\alpha_4\beta_2$ (alpha 4 beta 2) nicotinic receptor subtype, and preferably is an agonist of the $\alpha_4\beta_2$ nicotinic receptor subtype. Several compounds having such $\alpha_4\beta_2$ receptor subtype selectivity have been reported in the literature. An example of one such nicotinic compound is known as 7,8,9,10-tetrahydro-6,10-methano-6H-pyrazino(2,3-h)(3) benzazepine (also known as varenicline and in the form of varenicline tartrate which is the active ingredient of a product commercially marketed under the tradename Chantix or Champix by Pfizer). See, for example, Jorenby et al., JAMA, 296: 56-63 (2006) and US Pat. Pub. No. 2010/0004451 to Ahmed et al. Another representative compound is (2S,4E)-5-(5-isopropoxypyridin-3-yl)-N-methylpent-4-en-2-amine (also known as ispronicline or AZD-3480 of AstraZeneca or TC-1734 of Targacept, Inc. (Winston-Salem, N.C., USA)). See, for example, Dunbar et al., *Psychopharmacol.* (Berlin), 191: 919-929 (2007). Another representative compound is [3-(2(S))-azetidinylmethoxy)pyridine] dihydrochloride, (also known as A-85380). See, for example, Schreiber, *Psychopharmacol.*, 159:248-257 (2002). Another representative compound is (5aS,8S,10aR)-5a,6,9,10-Tetrahydro,7H,11H-8,10a-methanopyrido [2',3':5,6]pyrano[2,3-d]azepine (also known as SSR591813). See, for example, Cohen et al., *Neuroscience*, Pres. No. 811.5 (2002) and Cohen et al., *J. Pharmacol. Exp. Ther.*, 306: 407-420 (2003). Another representative compound is known as A-969933. See, for example, Zhu et al., *Biochem. Pharmacol.*, 78: 920 (2009). Other representative compounds are known as S35836-1 and S35678-1. See, for example, Lockhart et al., *Neuroscience*, Pres. No. 684.9 (2002). Yet other examples are compounds are those designated as 3-(5,6-Dichloro-pyridin-3-yl)-1S,5S-3,6-diazabicyclo[3.2.0]heptane (also known as Sofinicline or ABT-894) by Abbott Laboratories; AZD1446 by AstraZeneca and TC-6499 by Targacept, Inc. The foregoing cited references are incorporated herein by reference.

The compositions of the invention preferably include a form that is pharmaceutically effective and pharmaceutically acceptable. That is, the composition most preferably does not incorporate to any appreciable degree, or does not purposefully incorporate, components of tobacco, other than nicotine. As such, pharmaceutically effective and pharmaceutically acceptable compositions do not include tobacco, processed tobacco components, or many of the components of tobacco traditionally present within tobacco-containing cigarettes, cigars, pipes, or smokeless forms of tobacco products. Highly preferred compositions that are derived by extracting naturally-occurring nicotine from tobacco include less than 0.5 weight percent of tobacco components other than nicotine, more often less than about 0.25 weight percent, and typically are entirely absent or devoid of components of tobacco, processed tobacco components, or components derived from tobacco, other than nicotine, based on the total weight of the composition.

The pharmaceutical compositions of the invention may be conveniently made available in a unit dosage form, whereby such formulations may be prepared by any of the methods generally known in the pharmaceutical arts. Such methods of preparation comprise combining (by various methods) an active agent with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

The nicotine-containing pharmaceutical compositions of the invention can incorporate various pharmaceutically acceptable excipients. By "pharmaceutically acceptable carrier" or "pharmaceutically acceptable excipient" is intended a carrier or excipient that is conventionally used in the art to facilitate the storage, administration, and/or the healing effect of an active agent (e.g., a nicotinic compound). The carrier(s) are preferably pharmaceutically acceptable in the sense of being compatible with the other ingredients of the formulation and not unduly deleterious to the recipient thereof. A carrier may also reduce any undesirable side effects of the agent. See, Wang et al., *J. Parent. Drug Assn.*, 34(6): 452-462 (1980), which is incorporated herein by reference. Exemplary pharmaceutical excipients and/or additives suitable for use in the compositions according to the invention are listed in Remington: *The Science & Practice of Pharmacy*, 21$^{st}$ ed., Lippincott Williams & Wilkins (2006); in the *Physician's Desk Reference*, 64$^{th}$ ed., Thomson PDR (2010); and in *Handbook of Pharmaceutical Excipients*, 6$^{th}$ ed., Eds. Raymond C. Rowe et al., Pharmaceutical Press (2009), which are incorporated herein by reference.

The identity and quantity used of different excipients can vary, and the selection and amount of each excipient can depend upon factors such as the ultimate form and function of product that is desired. See, for example, the types of ingredients, relative amounts and combinations of ingredients, nicotine-containing formulations and preparation processes for nicotine-containing products set forth in U.S. Pat. No. 5,512,306 to Carlsson et al.; U.S. Pat. No. 5,525,351 to Dam; U.S. Pat. No. 5,549,906 to Santus; U.S. Pat. No. 5,711,961 to Reiner et al.; U.S. Pat. No. 5,811,126 to Krishnamurthy; U.S. Pat. No. 5,939,100 to Albrechtsen et al.; U.S. Pat. No. 6,024,981 to Khankari et al.; U.S. Pat. No. 6,083,531 to Humbert-Droz et al.; U.S. Pat. No. 6,090,401 to Gowan, Jr. et al.; U.S. Pat. No. 6,110,495 to Dam; U.S. Pat. No. 6,248,760 to Wilhelmsen; U.S. Pat. No. 6,280,761 to Santus; U.S. Pat. No. 6,426,090 to Ream et al.; U.S. Pat. No. 6,569,463 to Patel et al.; U.S. Pat. No. 6,583,160 to Smith et al.; U.S. Pat. No. 6,585,997 to Moro et al.; U.S. Pat. No. 6,676,959 to Andersson et al.; U.S. Pat. No. 6,893,654 to Pinney et al.; U.S. Pat. No. 7,025,983 to Leung et al. and U.S. Pat. No. 7,163,705 Johnson et al.; US Pat. Pub. No. 2003/0176467 to Andersson et al.; No. 2003/0235617 to Martino et al.; No. 2004/0096501 to Vaya et al.; No. 2004/0101543 to Liu et al.; No. 2004/0191322 to Hansson; No. 2005/0053665 to Ek et al.; No. 2005/0123502 to Chan et al.; No. 2008/0038209 to Andersen et al.; No. 2008/0286341 to Andersson et al.; No. 2009/0023819 to Axelsson; No. 2009/0092573 to Andersen; No. 2010/0004294 to Axelsson et al. and No. 2010/0061940 to Axelsson et al., which are incorporated herein by reference.

Representative types of excipients that are particularly useful for the manufacture of nicotine-containing products include fillers or carriers for active ingredients (e.g., calcium polycarbophil, microcrystalline cellulose, cornstarch, silicon dioxide or calcium carbonate), thickeners, film formers and binders (e.g., hydroxypropyl cellulose, hydroxypropyl methylcellulose, acacia, sodium alginate, xanthan gum and gelatin), buffers and pH control agents (e.g., magnesium oxide, magnesium hydroxide, potassium carbonate, sodium carbonate, potassium bicarbonate, sodium bicarbonate, or mixtures thereof), antiadherents (e.g., talc), glidants (e.g., colloidal silica), natural or artificial sweeteners (e.g., saccharin, acesulfame K, aspartame, sucralose, isomalt, lactose, mannitol, sorbitol, xylitol and sucrose), humectants (e.g., glycerin), preservatives and antioxidants (e.g., sodium benzoate and ascorbyl palm itate), surfactants (e.g., polysorbate 80), natural or artificial flavors (e.g., mint, cinnamon, cherry or other fruit flavors), dyes or pigments (e.g., titanium dioxide or D&C Yellow No. 10), and lubricants or processing aids (e.g, calcium stearate or magnesium stearate). Certain types of nicotine-containing products also can have outer coatings composed of ingredients capable of providing acceptable outer coatings (e.g., an outer coating can be composed of ingredients such as carnauba wax, and pharmaceutically acceptable forms of shellacs, glazing compositions and surface polish agents).

Representative compositions incorporating a source of nicotine and another nicotinic compound as active ingredients can have various types of formats and configurations, and as a result, the character, nature, behavior, consistency, shape, form, size and weight of the composition can vary. The shape of a representative composition can be generally spherical, cylindrical (e.g., ranging from the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, mini lozenge, capsule, caplet, pouch and gum types of products that traditionally have been employed for the administration of pharmaceutical types of products. The general nature of a representative composition can be soft or hard to the touch or of intermediate softness or hardness; and as such, the composition can be considered to be malleable, flexible, chewy, resilient, brittle, or the like. When administered orally, various components of the product can be considered to be readily dispersible or slow to disperse, or those various components can dissolve at varying rates (e.g., from relatively fast to relatively slow). As a result, for compositions ingested by insertion in the mouth of the human subject, the release rate of active ingredient during use of the product can vary from relatively fast to relatively slow, depending upon factors such as the design of the product and the use of product by the subject using that product. See also, by way of example, the types of products proposed in U.S. Pat. No. 4,655,231 to Ray et al.; U.S. Pat. No. 5,147,654 to Place et al.; U.S. Pat. No. 5,543,424 to Carlsson et al.; U.S. Pat. No. 6,268,386 to Thompson; U.S. Pat. No. 6,319,510 to Yates; U.S. Pat. No. 6,488,953 Halliday et al.; U.S. Pat. No. 6,709,671 to Zerbe et al.; U.S. Pat. No. 7,025,983 to Leung et al.; U.S. Pat. No. 7,105,173 to Rolling; U.S. Pat. No. 7,115,297 to Stillman; U.S. Pat. No. 7,435,749 to Knight and U.S. Pat. No. 7,491,406 to Leung et al.; and US Pat. Pub. No. 2004/0191322 to Hansson; No. 2006/0198873 to Chan et al.; No. 2006/0240087 to Houze et al.; No. 2006/0204559 to Bess et al.; No. 2007/0269492 to Steen et al.; No. 2008/0020050 to Chau et al.; No. 2008/0286340 to Andersson et al.; No. 2008/0292683 to Sanghvi et al. and No. 2009/0004248 to Bunick et al., which are incorporated herein by reference.

Compositions of the present invention may include short-term, rapid-onset, rapid-offset, controlled release, sustained release, delayed release, and pulsatile release formulations, providing the formulations achieve administration of a nicotinic compound as described herein. See Remington's *Pharmaceutical Sciences*, 18$^{th}$ ed.; Mack Publishing Company, Eaton, Pa., (1990), which is incorporated herein by reference.

Solid dosage forms may be formulated so as to provide a delayed release of the active agent (i.e., the nicotinic compounds), such as by application of a coating. Delayed release coatings are known in the art, and dosage forms containing such may be prepared by any known suitable method. Such methods generally involve application of a delayed release coating composition after preparation of the solid dosage form (e.g., a tablet or caplet). Application of the coating may be implemented using methods such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also provide sustained release (i.e., releasing the active agent over a prolonged period of time), and may or may not also provide delayed release. Sustained release formulations are known in the art and are generally prepared by dispersing the active ingredient within a matrix of a gradually degradable or hydrolyzable material, such as an insoluble plastic, a hydrophilic polymer, or a fatty compound. Alternatively, a solid dosage form may be coated with such a material.

The manners and methods used to formulate and manufacture the composition can vary. Typical conditions associated with manufacture of pharmaceutical types of products include control of heat and temperature (i.e., the degree of heat to which the various ingredients are exposed during manufacture and the temperature of the manufacturing environment), moisture content (e.g., the degree of moisture present within individual ingredients and within the final composition), humidity within the manufacturing environment, airflow experienced by the various ingredient during the manufacturing process, and other similar types of factors. Additionally, various process steps involved in product manufacture can involve selection of certain solvents and processing aids, use of heat and radiation, refrigeration and cryogenic conditions, and the like. The manufacturing conditions also can be controlled due to selection of the form of various ingredients (e.g., solid, liquid or gas), particle size or crystalline nature of ingredients of solid form, concentration of ingredients in liquid form, or the like. Ingredients can be processed into the desired composition by techniques such as extrusion, compression, spraying, and the like.

The manners and methods for incorporating the nicotinic compounds (i.e., the source of nicotine and the other nicotinic compound) into the nicotine-containing composition can vary. The location of each of the active ingredients within the composition can vary. The nicotinic compounds can be located throughout the composition or in selected regions of the composition (e.g., homogeneously throughout the composition, in an outer coating of the composition or in the region of the composition occupied by nicotine or in selected layer(s) of a laminated composition). As such, certain regions of the composition can be essentially devoid of any or all nicotinic compounds, there can exist a concentration gradient of various nicotinic compounds within or throughout the composition, or a certain region of the composition can have a relatively high concentration of some or all of the nicotinic compounds relative to other regions of that composition. Compositions can be co-extruded, laminated or formed so as to have sandwich-type forms; and hence the location of nicotine, other nicotinic compound and other ingredients can be controlled in order to provide the desired features such as performance, behavior, interaction or non-interaction with other ingredients, storage stability, and the like. In addition, mixtures of component ingredients can be formulated and manufactured into core/shell types of configurations (e.g., gum or lozenge types of products that have an inner region and at least one additional overlayer), with the various regions of such products having differing overall compositions or properties. Thus, for example, any or all of the other nicotinic compounds can have relatively high concentrations towards the inner region of the product, or relatively high concentrations towards the outer region of the product.

The other nicotinic compound can be mixed with the source of nicotine (e.g., with nicotine salts), and incorporated into the composition as a mixture. Various forms of nicotine and the other nicotinic compound also can be introduced into the composition at different times or stages of the manufacturing process, or in combination with different ingredients employed in the manufacturing process. Alternatively, the other nicotine compound can be segregated from the nicotine within the composition (e.g., by physically locating the other nicotinic compound and nicotine at separate locations within the composition, or by segregating the nicotinic compound and nicotine using encapsulation or other types of chemical means to separate those components).

In one embodiment, at least one of nicotine and the nicotinic compound can be sorbed onto a porous particulate carrier material, such as microcrystalline cellulose (MCC). In one embodiment, the MCC materials so employed have an average particle size range of about 15 to about 250 microns. Exemplary MCC materials include various grades of AVICEL® and VIVACEL® materials. See, for example, US Pat. Pub. No. 2004/0191322 to Hansson, which is incorporated herein by reference. Thus, in certain embodiments, multiple forms of nicotinic compounds can be sorbed onto the particulate carrier including any of the various nicotinic compound combinations discussed herein, such as nicotine free base combined with a nicotinic compound salt, two nicotinic salts (e.g., a nicotine levulinate/nicotine tartrate mixture or a nicotine levulinate/nicotine bitartrate mixture), and the like. The nicotine compound can be sorbed onto the particulate carrier by, for example, dissolving the nicotinic compound in a hydrophilic solvent (e.g., water, alcohol, or mixtures thereof) and combining the solution with the particulate carrier, followed by drying to remove the solvent. The particulate carrier material with sorbed nicotinic compound can be combined with other carriers or excipients in order to provide a composition adapted for oral or nasal delivery of the active ingredients.

In use, the compositions of the present invention most preferably are administered by oral ingestion. For example, nicotine-containing compositions can be administered and employed using the manners and methods typically used for the administration of traditional types of nicotine containing gums, lozenges, pouch product and sprays.

One particularly preferred type of a representative composition incorporating a source of nicotine and another nicotinic compound as active ingredients, and that provides nicotine delivery in a non-inhalable form, has the form of a gum or other type of similarly chewable product. Gum forms of product include gum base (e.g., typically the types of pharmaceutically acceptable gum bases available from sources such as Gum Base Co. S.p.a., Wm. J. Wrigley Jr. Company or Gumlink A/S). See, for example, the types of nicotine-containing gums, gum formulations, gum formats and configurations, gum characteristics and techniques for formulating or manufacturing gums are set forth in U.S. Pat. No. 3,845,217 to Ferno et al.; U.S. Pat. No. 3,877,468 to Lichtneckert et al.; U.S. Pat. No. 3,901,248 to Lichtneckert et al.; U.S. Pat. No. 5,154,927 to Song et al.; U.S. Pat. No. 6,322,806 to Ream et al.; U.S. Pat. No. 6,344,222 to Cherukuri et al.; U.S. Pat. No. 6,355,265 to Ream et al.; U.S. Pat. No. 6,358,060 to Pinney et al.; U.S. Pat. No. 6,773,716 to Ream et al.; U.S. Pat. No. 6,893,654 to Pinney et al.; U.S. Pat. No. 7,101,579 Athanikar et al.; U.S. Pat. No. 7,163,705 to Johnson et al. and U.S. Pat. No. 7,208,186 to Norman et al.; US Pat. Pub. No. 2004/0194793 to Lindell et al.; No. 2006/0099300 to Andersen et al.; No. 2006/0121156 to Andersen et al.; No. 2006/0165842 to Andersen et al.; No. 2006/0204451 to Salini; No. 2006/0246174 to Andersen et al.; No. 2006/0275344 to Mody et al.; No. 2007/0014887 to Cherukuri et al.; No. 2007/0269386 to Steen et al. and No. 2009/0092573 to Andersen and PCT WO 2007/104574 to Axelsson et al.; which are incorporated herein by reference. The amount of composition contained within each piece of unit of gum type of product can vary. For example, representative unit or gum types of products generally weigh at least about 0.5 g, often at least about 1 g, and frequently at least about 1.5 g, of composition; while the weight of such types of products generally does not exceed about 3 g, often does not exceed about 2.5 g, and frequently does not exceed about 2 g. The time period over which the gum piece can be chewed can vary; and typically, each piece of gum is chewed for at least about 5 minutes, often at least about 10 minutes, while each piece of gum typically is chewed for up to about 40 minutes, often up to about 30 minutes.

Another particularly preferred type of a representative composition incorporating a source of nicotine and another nicotinic compound as active ingredients, and that provides nicotine delivery in a non-inhalable form, has the form of a lozenge, tablet, microtab, or other type tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen and U.S. Pat. No. 7,374,779; US Pat. Pub. No. 2001/0016593 to Wilhelmsen; No. 2004/0101543 to Liu et al.; No. 2006/0120974 to Mcneight; No. 2008/0020050 to Chau et al. and No. 2009/0081291 to Gin et al.; PCT WO 91/09599 to Carlsson et al. and PCT WO 2007/104575 to Axelsson; which are incorporated herein by reference. The amount of composition contained within each piece or unit of lozenge type of product can vary. For example, representative units of lozenge types of products generally weigh at least about 100 mg, often at least about 200 mg, and frequently at least about 300 mg, of composition; while the weight of such types of products generally does not exceed about 1.5 g, often does not exceed about 1 g, and frequently does not exceed about 0.75 g.

Another particularly preferred type of a representative composition incorporating a source of nicotine and another nicotinic compound as active ingredients, and that provides nicotine delivery in a non-inhalable form, has the form of a pouch or sachet type of product. See, for example, the types of pouch materials and nicotine-containing formulations set forth in PCT WO 2007/104575 to Axelsson et al.; which is incorporated herein by reference. See also, for example, the types of pouch materials and pouch manufacturing techniques (e.g., filling and sealing techniques) set forth in US Pat. Pub. No. 2010/0018539 to Brinkley et al.; which is incorporated herein by reference. The amount of composition contained within each pouch can vary. For example, representative pouch products generally contain at least about 75 mg, often at least about 100 mg, and frequently at least about 150 mg, of composition; while the amount of composition contained in representative pouch products generally does not exceed about 500 mg, often does not exceed about 400 mg, and frequently does not exceed about 300 mg.

The amount of nicotine active ingredient within the overall composition can vary. For a composition intended for oral consumption by insertion into the mouth of the subject (e.g., chewable piece of gum product, a lozenge, a pouch product, or the like), the amount of nicotine within each dosage piece or unit typically is at least about 0.5 mg, generally is at least 1 mg, often is at least about 1.5 mg and frequently is at least about 2 mg; while the amount of nicotine within each piece typically does not exceed about 10 mg, generally does not exceed about 8 mg, often does not exceed about 6 mg and frequently does not exceed about 5 mg. Exemplary types of such products incorporate about 2 mg, about 2.5 mg, about 3.5 mg and about 4 mg of nicotine per piece or unit (calculated as nicotine free base).

The amount of the other nicotinic compound active ingredient within the overall composition can vary. For a composition intended for oral consumption by insertion into the mouth of the subject (e.g., chewable piece of gum product, a lozenge, a pouch product, or the like), the amount of other nicotinic compound within each dosage piece or unit typically does not exceed about 100 mg, generally does not exceed about 75 mg, often does not exceed about 50 mg. The amount of other nicotinic compound within each dosage piece or unit generally is at least about 0.1 mg, typically is at least about 0.5 mg and often is at least 1 mg. Depending upon the pharmacological effect provided by the other nicotinic compound, the amount of that compound within each dosage piece or unit typically can be at least about 2 mg and often can be at least about 5 mg. Exemplary types of such products incorporate about 0.5 mg, about 1 mg, about 25 mg and about 50 mg of other nicotinic compound per piece or unit.

Another particularly preferred type of a representative composition incorporating a source of nicotine and another nicotinic compound active ingredient has the form of a spray. See, for example, the types of spray materials and nicotine-containing spray formulations set forth in U.S. Pat. No. 4,579,858 to Ferno et al.; U.S. Pat. No. 5,656,255 to Jones; U.S. Pat. No. 6,024,097 to Von Wielligh and U.S. Pat. No. 6,596,740 to Jones; US Pat. Pub. No. 2003/0159702 to Lindell et al. and No. 2007/0163610 to Lindell et al.; EP 1458388 to Lindell et al.; PCT WO 2006/100075 to Axelsson and PCT WO 2008/037470 to Axelsson et al.; which are incorporated herein by reference. Preferred spray form products produce sprays or mists using nebulizers or other types of devices for producing aerosols by mechanical means. Preferred spray types of products employ liquid solvents or carriers (e.g., water or water/ethanol mixtures) that contain nicotine and the other nicotinic compound. The concentration of the nicotine within the liquid spray formulation can vary, but typically is in the range of about 0.5 percent to about 5 percent, often about 1 percent to about 3 percent, based on the total weight of the liquid formulation. Depending upon the identity of the other nicotinic compound incorporated within the spray formulation, the concentration of the other nicotinic compound within the liquid spray formulation typically is in the range of about 0.1 percent to about 15 percent, often about 0.2 percent to about 10 percent, based on the total weight of the liquid formulation.

Although the compositions of the invention are preferably non-inhalable, it is possible to formulate the above-noted combinations of nicotinic compounds in a form capable of pulmonary delivery using various types of inhalation devices and vapor delivery systems designed to deliver an active agent to the lungs as opposed to buccal, sublingual, or nasal delivery. See, for example, the types of inhalable formulations and vapor delivery devices and systems set forth in U.S. Pat. No. 4,284,809 to Ray; U.S. Pat. No. 4,800,903 to Ray et al.; U.S. Pat. No. 5,167,242 to Turner et al.; U.S. Pat. No. 6,098,632 to Turner et al.; U.S. Pat. No. 6,234,169 to Bulbrook et al. and U.S. Pat. No. 6,874,507 to Farr; US Pat. Pub. No. 2004/0034068 to Warchol et al; No. 2006/0018840 to Lechuga-Ballesteros; No. 2008/0302375 to Andersson et al. and No. 2009/0005423 to Gonda; and EP 1,618,803 to Hon, which are incorporated herein by reference.

Though not preferred, compositions of the present invention can be administered in a transdermal manner. See, for example, the types of transdermal delivery technologies set forth in U.S. Pat. No. 4,597,961 to Etscom; U.S. Pat. No. 5,298,257 to Bannon et al.; U.S. Pat. No. 5,603,947 to Wong et al.; U.S. Pat. No. 5,834,011 to Rose et al.; U.S. Pat. No. 6,165,497 to Osborne et al. and U.S. Pat. No. 6,676,959 to Anderson et al and PCT WO 2007/012963 to Johnson et al.; which are incorporated herein by reference.

For compositions of the present invention, the intended dose of the nicotine active ingredient can vary. The overall dose of that active ingredient can depend upon factors such as the weight of the subject ingesting the composition, the condition, disease or disorder being treated, the state or severity of the condition, disease or disorder being treated, the desired pharmacological effect, or other such factors. Typically, the amount of nicotine active ingredient administered to a subject per day is at least about 2 mg, often is at least about 4 mg, and frequently is at least about 10 mg. Typically, the amount of nicotine active ingredient administered to a subject per day does not exceed about 60 mg, often does not exceed about 50 mg, and frequently does not exceed about 40 mg. The dose of nicotine, whether on a per dose or on an overall daily basis, is such that the subject does not experience untoward side effects resulting from overexposure of that subject to nicotine. See also, for example, the types of dosing regimens and administration techniques set forth in U.S. Pat. No. 6,660,754 to Kyle et al. and US Pat. Pub. No. 2004/0006113 to Sachs; No. 2005/0214229 to Pinney et al. and No. 2008/0124283 to Andersen and PCT WO 2007/104573 to Axelsson et al.; which are incorporated herein by reference.

For compositions of the present invention, the intended dose of the other nicotinic compound active ingredient can vary. The overall dose of that active ingredient can depend upon factors such as the weight of the subject ingesting the composition, the condition being treated, the state or severity of the disease or disorder being treated, the desired pharmacological effect, the potency of that active ingredient, the amount of nicotine present in the composition in combination with that active ingredient, or other such factors. Typically, the amount of other nicotinic compound active ingredient administered to a subject per day does not exceed about 75 mg, and often does not exceed about 50 mg. For certain other nicotinic compound active ingredients, the amount administered to a subject per day typically does not exceed 10 mg, and often does not exceed about 5 mg. A highly preferred dose of the other nicotinic compound is such that sufficient compound is administered to provide the desired CNS effect (e.g., due to the effect of that compound at nAChRs within the CNS), while not sufficiently high so as to cause provide side effects associated with toxicity or unwanted side effects resulting from significant interaction of that compound at nAChRs within the PNS.

For compositions of the present invention, the amount nicotine active ingredient relative the amount of other nicotinic compound active ingredient in each dosage source or unit can vary. In one regard, the amount of nicotine active ingredient can be less than, approximately equal to or exceed the amount of the other nicotinic compound active ingredient, on a weight basis. For example, a piece gum or lozenge can incorporate about 1 to about 5 mg of nicotine, and about 0.1 mg to about 2 mg of either a compound known as varenicline or an agonist of an $\alpha_7$ nicotinic receptor subtype or an $\alpha_4\beta_2$ nicotinic receptor subtype. In one regard, the amount of the other nicotinic compound active ingredient can exceed the amount of the nicotine active ingredient, on a weight basis. For example, a piece gum or lozenge can incorporate about 1 to about 5 mg of nicotine, and about 10 mg to about 75 mg of either a compound known as AZD-3480 or a compound known as TC-5619.

The dose of the combination of active ingredients is that amount effective to treat some symptoms of, or prevent occurrence of the symptoms of, the condition, disease or disorder from which the subject or patient suffers. By "effective amount," "therapeutic amount" or "effective dose" is meant that amount sufficient to elicit the desired pharmacological or therapeutic effects, thus resulting in effective prevention or treatment of the condition, disease or disorder. Thus, an effective amount of active ingredients is an amount sufficient to enter relevant regions of the body (e.g., to pass across the blood-brain barrier of the subject), to bind to relevant receptor sites in the CNS and PNS of the subject, and to elicit neuropharmacological effects (e.g., elicit neurotransmitter secretion, thus resulting in effective prevention or treatment of the condition, disease or disorder). Prevention of the disorder is manifested by delaying the onset of the symptoms of the condition, disease or disorder. Treatment of the disorder is manifested by a decrease in the symptoms associated with the condition, disease or disorder or an amelioration of the reoccurrence of the symptoms thereof.

In use, the sources of nicotine and the other nicotinic compound active ingredients are administered in combination with one another. For example, pharmaceutically effective amounts of each active ingredient preferably are incorporated into a single dosage source or unit (e.g., an individual piece of gum, a single lozenge, or the like, and preferably by ingestion by oral means). The nicotine active ingredient is an example of an ingredient that, at the dose administered, binds to and activates various nicotinic receptor subtypes located in both the CNS and the PNS. Hence, at the dose administered, the nicotine active ingredient does not discriminate (from the standpoint of its ability to undergo binding and elicit activation) among the various nAChRs expressed in the CNS and PNS. As such, administration of nicotine introduces CNS effects as well as PNS effects at peripheral sites (e.g., neuromuscular, cardiovascular and gastrointestinal sites). Conversely, the other nicotinic compound active ingredient is selective to certain nAChRs expressed in the CNS. That is, the other nicotinic compound active ingredient, at the dose administered, exhibits an affinity to bind to and activate nicotinic receptor subtypes located in the CNS. Thus, administration of the combination of nicotinic compound active ingredients provides CNS effects (e.g., as a result of the administration of the combination of nicotine and the other nicotinic compound) and PNS effects (e.g., principally or virtually entirely as a result of the administration of nicotine). As such, it is highly preferred that the other nicotinic compound be administered within the relevant "therapeutic window" or within the "therapeutic index" of that compound, and that the dose of that other nicotinic compound be within a dosage range sufficient that the compound elicits a desirable response within the CNS while effects of that compound upon the PNS are avoided to any significant extent. See, for example, Bencherif et al., *J. Pharmacol. Exp. Ther.*, 279: 1413-1421 (1996) and U.S. Pat. No. 5,583,140 to Bencherif et al.; which are incorporated herein by reference.

The compositions of the present invention can be used for treatment of a wide variety of conditions, diseases and disorders. The compositions can be used to treat those types of conditions, diseases and disorders that have been reported to be treatable through the use or administration of nicotine. As such, the compositions can be used to treat various CNS conditions, diseases and disorders, and the compositions also can be used as smoking cessation aids (i.e., as components of NRT).

The following examples are provided in order to further illustrate the invention but should not be construed as limiting the scope thereof. Unless otherwise noted, all parts and percentages are by weight.

EXAMPLE 1

A lozenge generally similar in shape and form to a lozenge incorporating 0.5 mg varenicline in the form of the tartrate salt of the active ingredient of a product commercially marketed under the tradename Chantix by Pfizer Incorporated is produced using generally similar excipient ingredients and processing conditions used for the manufacture of the commercial lozenge, except that the varenicline active ingredient replaced by a mixture of nicotine polacrilex and varenicline. The amount of nicotine polacrilex incorporated into each lozenge is such that the amount of nicotine active ingredient within each lozenge from that source is 2 mg; and the amount of varenicline incorporated into each lozenge is such that the amount of that active ingredient within each lozenge is 0.5 mg. As such, each lozenge (i.e., each dosing unit) incorporates both nicotine and a nicotinic compound purported to have selectivity to the $\alpha_4\beta_2$ nicotinic receptor subtype.

EXAMPLE 2

A lozenge generally similar in shape and form to a lozenge incorporating 0.5 mg varenicline and commercially available as Chantix is produced using generally similar excipient ingredients and processing conditions used for the manufacture of the commercial lozenge, except that the varenicline active ingredient replaced by a mixture of nicotine polacrilex and varenicline. The amount of nicotine polacrilex incorporated into each dosage unit (i.e., each lozenge) is such that the amount of nicotine active ingredient within each lozenge from that source is 3 mg; and the amount of varenicline incorporated into each lozenge is such that the amount of that active ingredient within each lozenge is 0.1 mg. As such, each lozenge (i.e., each dosing unit)

EXAMPLE 3

A gum generally similar in shape and form to a nicotine-containing gum incorporating 4 mg of nicotine and commercially available as Nicorette Original Gum (distributed by GlaxoSmithKline Consumer Healthcare, L.P.) is produced using generally similar excipient ingredients and processing conditions used for the manufacture of the commercial gum, except that the nicotine polacrilex thereof is replaced by a mixture of nicotine polacrilex and a compound known as varenicline (e.g., in the form of the tartrate salt found in Chantix). The amount of nicotine polacrilex incorporated into each chewing piece of gum is such that the amount of nicotine active ingredient within each chewing piece from that source is 3 mg; and the amount of varenicline active ingredient incorporated into each chewing piece of gum is such that the amount of active ingredient within each chewing piece from that source is 1 mg. As such, each chewing piece of the gum product (i.e., each dosing unit) incorporates both nicotine and a nicotinic compound purported to have selectivity to the $\alpha_4\beta_2$ nicotinic receptor subtype.

EXAMPLE 4

A gum generally similar in shape and form to a nicotine-containing gum incorporating 4 mg of nicotine and commercially available as Nicorette Original Gum (distributed by GlaxoSmithKline Consumer Healthcare, L.P.) is produced using generally similar excipient ingredients and processing conditions used for the manufacture of the commercial gum, except that the nicotine polacrilex thereof is replaced by a mixture of nicotine polacrilex and a compound known as varenicline (e.g., in the form of the tartrate salt found in Chantix). The amount of nicotine polacrilex incorporated into each dosage unit (i.e., into each chewing piece of gum) is such that the amount of nicotine active ingredient within each chewing piece from that source is 3 mg; and the amount of varenicline active ingredient incorporated into each chewing piece of gum is such that the amount of active ingredient within each chewing piece from that source is 0.2 mg. As such, each chewing piece of the gum product (i.e., each dosing unit) incorporates both nicotine and a nicotinic compound purported to have selectivity to the $\alpha_4\beta_2$ nicotinic receptor subtype.

EXAMPLE 5

A gum generally similar in shape and form to a nicotine-containing gum incorporating 4 mg of nicotine and commercially available as Nicorette Original Gum (distributed by GlaxoSmithKline Consumer Healthcare, L.P.) is produced using generally similar excipient ingredients and processing conditions used for the manufacture of the commercial gum, except that the nicotine polacrilex thereof is replaced by a mixture of nicotine polacrilex and a compound of Targacept, Inc, (Winston-Salem, N.C., USA), known as TC-5619. In one aspect, the amount of nicotine polacrilex incorporated into each chewing piece of gum is such that the amount of nicotine active ingredient within each chewing piece from that source is 3 mg; and the amount of TC-5619 (active ingredient in free base form) incorporated into each chewing piece of gum is such that the amount of active ingredient within each chewing piece from that source is 1 mg. In a second aspect, the amount of nicotine polacrilex incorporated into each chewing piece of gum is such that the amount of nicotine active ingredient within each chewing piece from that source is 3 mg; and the amount of TC-5619 (active ingredient in free base form) incorporated into each chewing piece of gum is such that the amount of active ingredient within each chewing piece from that source is 5 mg. In a third aspect, the amount of nicotine polacrilex incorporated into each chewing piece of gum is such that the amount of nicotine active ingredient within each chewing piece from that source is 3 mg; and the amount of TC-5619 (active ingredient in free base form) incorporated into each chewing piece of gum is such that the amount of active ingredient within each chewing piece from that source is 25 mg. As such, each chewing piece of the gum product (i.e., each dosing unit) incorporates nicotine and a nicotinic compound purported to have selectivity to the $\alpha_7$ nicotinic receptor subtype.

EXAMPLE 6

A gum generally similar in shape and form to a nicotine-containing gum incorporating 4 mg of nicotine and commercially available as Nicorette Original Gum (distributed by GlaxoSmithKline Consumer Healthcare, L.P.) is produced using generally similar excipient ingredients and processing conditions used for the manufacture of the commercial gum, except that the nicotine polacrilex thereof is replaced by a mixture of nicotine polacrilex and a compound of AstraZeneca known as AZD-3480 ((2S,4E)-5-(5-iso-propoxypyridin-3-yl)-N-methylpent-4-en-2-amine). In one aspect, the amount of nicotine polacrilex incorporated into each chewing piece of gum is such that the amount of nicotine active ingredient within each chewing piece from that source is 3 mg; and the amount of AZD-3480 incorporated into each chewing piece of gum is such that the amount of active ingredient within each chewing piece from that source is 25 mg. In another aspect, the amount of nicotine polacrilex incorporated into each chewing piece of gum is such that the amount of nicotine active ingredient within each chewing piece from that source is 3 mg; and the amount of AZD-3480 incorporated into each chewing piece of gum is such that the amount of active ingredient within each chewing piece from that source is 50 mg. As such, each chewing piece of the gum product (i.e., each dosing unit) incorporates nicotine and a nicotinic compound purported to have selectivity to the $\alpha_4\beta_2$ nicotinic receptor subtype.

EXAMPLE 7

A coated gum generally similar in shape and form to a nicotine-containing gum incorporating 4 mg of nicotine and commercially available as Nicorette Fruit Chill Gum (distributed by Walgreen Co.) is produced using generally similar excipient ingredients and processing conditions used for the manufacture of the commercial gum, except that the nicotine polacrilex thereof is replaced by a mixture of nicotine polacrilex and a compound of Targacept, Inc. known as TC-5619. In one aspect, the amount of nicotine polacrilex incorporated into each chewing piece of gum is such that the amount of nicotine active ingredient within each chewing piece from that source is 3 mg; and the amount of TC-5619 (active ingredient in free base form) incorporated into each chewing piece of gum is such that the amount of active ingredient within each chewing piece from that source is 1 mg. In a second aspect, the amount of nicotine polacrilex incorporated into each chewing piece of gum is such that the amount of nicotine active ingredient within each chewing piece from that source is 3mg; and the amount of TC-5619 (active ingredient in free base form) incorporated into each chewing piece of gum is such that the amount of active ingredient within each chewing piece from that source is 5mg. In a third aspect, the amount of nicotine polacrilex incorporated into each chewing piece of gum is such that the amount of nicotine active ingredient within each chewing piece from that source is 3 mg; and the amount of TC-5619 (active ingredient in free base form) incorporated into each chewing piece of gum is such that the amount of active ingredient within each chewing piece from that source is 25 mg. As such, each chewing piece of the gum product (i.e., each dosing unit) incorporates nicotine and a nicotinic compound purported to have selectivity to the $\alpha_7$ nicotinic receptor subtype.

EXAMPLE 8

A coated gum generally similar in shape and form to a nicotine-containing gum incorporating 4 mg of nicotine and commercially available as Zonnic (distributed by Niconovum AB, Sweden) is produced using generally similar excipient ingredients and processing conditions used for the manufacture of the commercial gum, except that the nicotine and microcrystalline cellulose thereof is replaced by a mixture of nicotine/microcrystalline cellulose and a compound of AstraZeneca known as AZD-3480. In one aspect, the amount of nicotine/microcrystalline cellulose incorporated into each chewing piece of gum is such that the amount of nicotine active ingredient within each chewing piece from that source is 3 mg; and the amount of AZD-3480 incorporated into each chewing piece of gum is such that the amount of active ingredient within each chewing piece from that source is 25 mg. In another aspect, the amount of nicotine/microcrystalline cellulose incorporated into each chewing piece of gum is such that the amount of nicotine active ingredient within each chewing piece from that source is 3 mg; and the amount of AZD-3480 incorporated into each chewing piece of gum is such that the amount of active ingredient within each chewing piece from that source is 50 mg. As such, each chewing piece of the gum product (i.e., each dosing unit) incorporates nicotine and a nicotinic compound purported to have selectivity to the $\alpha_4\beta_2$ nicotinic receptor subtype.

EXAMPLE 9

A gum product generally similar in shape and form, and produced using generally similar excipient ingredients and processing conditions, to the nicotine-containing gum designated as Composition A as set forth in Example 6 of PCT WO 2007/104574 to Axelsson et al. is provided, except that, in addition to the nicotine ingredient of each gum piece, sufficient compound of AstraZeneca known as AZD-3480 is incorporated into each gum piece such that the amount of active ingredient within each dosage unit from that source is 25 mg. As such, each chewing piece of the gum product (i.e., each dosing unit) incorporates nicotine and a nicotinic compound purported to have selectivity to the $\alpha_4\beta_2$ nicotinic receptor subtype.

EXAMPLE 10

A gum product generally similar in shape and form, and produced using generally similar excipient ingredients and processing conditions, to the nicotine-containing gum designated as Composition B, as set forth in Example 6 of PCT WO 2007/104574 to Axelsson et al. is provided, except that, in addition to the nicotine ingredient of each gum piece, sufficient compound of Targacept, Inc. known as TC-5619 is incorporated into each gum piece such that the amount of TC-5619 active ingredient within each gum piece is 25 mg. As such, each chewing piece of the gum product (i.e., each dosing unit) incorporates nicotine and a nicotinic compound purported to have selectivity to the $\alpha_7$ nicotinic receptor subtype.

EXAMPLE 11

A lozenge generally similar in shape and form to a nicotine-containing lozenge incorporating 2.5 mg of nicotine is produced using generally similar excipient ingredients and processing conditions used for the manufacture of that lozenge set forth in Table 1 of Example 3 of PCT WO 2007/104575 to Axelsson, except that, in addition to the nicotine bitartrate dihydrate ingredient of that lozenge, sufficient compound of Targacept, Inc. known as TC-5619 is incorporated into each lozenge such that the amount of nicotine active ingredient within each lozenge is 2.5 mg and the amount of TC-5619 active is 25 mg. As such, each lozenge (i.e., each dosing unit) incorporates nicotine and a nicotinic compound purported to have selectivity to the $\alpha_7$ nicotinic receptor subtype.

EXAMPLE 12

A lozenge generally similar in shape and form to a nicotine-containing lozenge incorporating 2 mg of nicotine and commercially available as NiQuitin (distributed by GSK Consumer Healthcare A/S) is produced using generally similar excipient ingredients and processing conditions used for the manufacture of the commercial lozenge, except that the nicotine bitartrate active ingredient replaced by a mixture of nicotine bitartrate and a compound of Targacept, Inc. known as TC-5619 The amount of nicotine bitartrate incorporated into each lozenge is such that the amount of nicotine active ingredient within each lozenge from that source is 2 mg; and the amount of TC-5619 incorporated into each lozenge is such that the lozenge product incorporates 25 mg of TC-5619. As such, each lozenge (i.e., each dosing unit) incorporates nicotine and a nicotinic compound purported to have selectivity to the $\alpha_7$ nicotinic receptor subtype.

EXAMPLE 13

A pouch type of product similar in shape and form to a nicotine-containing pouch commercially available as Zonnic (distributed by Niconovum A.B.) is produced using generally similar pouch material, excipient ingredients and processing conditions used for the manufacture of the commercial pouch, except that the nicotine/microcrystalline cellulose ingredient thereof is replaced by a mixture of a compound known as TC-5619 and nicotine/microcrystalline cellulose. The amount of nicotine/microcrystalline cellulose incorporated into each pouch is such that the amount of nicotine active ingredient within each pouch from that source is the same as the commercially available pouch, and the amount of TC-5619 incorporated into the pouch is such that 25 mg of TC-5619 active ingredient is incorporated into the pouch. As such, each pouch (i.e., each dosing unit)

incorporates nicotine and a nicotinic compound purported to have selectivity to the $\alpha_7$ nicotinic receptor subtype.

EXAMPLE 14

Pouch type products generally similar in shape and form to a nicotine-containing pouches set forth as snuff bag compositions E-J in Example 1 of PCT WO 2007/104573 to Axelsson et al. are produced using generally similar excipient ingredients and processing conditions used for the manufacture of those pouch type products, except that 25 mg of a compound of AstraZeneca known as AZD-3480 also is incorporated within the formulation employed to manufacture that pouch product. Thus, both nicotine and another nicotinic compound are active ingredients incorporated into each dosage unit (i.e., within each pouch or bag). As such, each pouch (i.e., each dosing unit) incorporates nicotine and a nicotinic compound purported to have selectivity to the $\alpha_4\beta_2$ nicotinic receptor subtype.

EXAMPLE 15

A spray formulation generally similar to a nicotine-containing spray formulation designated as Composition A and set forth in Example 1 of PCT WO 2006/100075 to Axelsson is prepared, except that, in addition, 0.2 mg of varenicline active ingredient is incorporated into that formulation. As such, the spray incorporates both nicotine and a nicotinic compound purported to have selectivity to the $\alpha_4\beta_2$ nicotinic receptor subtype.

EXAMPLE 16

A spray formulation generally similar to a nicotine-containing spray formulation commercially available as Zonnic (distributed by Niconovum A.B.) is prepared, except that, in addition, 10 mg of a compound of AstraZeneca known as AZD-3480 is incorporated into that formulation. Thus, nicotine and another nicotinic compound are the active ingredients incorporated into each dosage unit (i.e., within the spray formulation). As such, the spray incorporates both nicotine and a nicotinic compound purported to have selectivity to the $\alpha_4\beta_2$ nicotinic receptor subtype.

A spray formulation generally similar to a nicotine-containing spray formulation commercially available as Zonnic (distributed by Niconovum A.B.) is prepared, except that, in addition, 10 mg of a compound of Targacept, Inc, known as TC-5619 is incorporated into that formulation. Thus, nicotine and another nicotinic compound are the active ingredients incorporated into each dosage unit (i.e., within the spray formulation). As such, the spray incorporates both nicotine and a nicotinic compound purported to have selectivity to the $\alpha_7$ nicotinic receptor subtype.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

I claim:

1. A composition comprising:
    nicotine; and
    an agonist or pharmaceutically acceptable salt thereof, having selectivity to an $\alpha_7$ nicotinic receptor subtype, wherein the agonist is selected form the group consisting of N-[(2S,3S)-2-(pyridin-3-ylmethyl)-1-azabicyclo [2.2.2]oct-3-yl]-1-benzofuran-2-carboxamide,(5aS,8S,10aR)-5a,6,9,10-Tetrahydro,7H,11H-8,10a-methanopyrido[2',3':5,6]pyrano[2,3-d]azepine, 1,4-Diazabicyclo[3.2.2]nonane-4-carboxylic acid, 4-bromophenyl ester, 3-[(3E)-3-[(2,4-dimethoxyphenyl)methylidene]-5,6-dihydro-4H-pyridin-2-yl]pyridine, 2-methyl-5-(6-phenyl-pyridazin-3-yl)-octahydro-pyrrolo[3,4-c]pyrrole, (5S)-spiro[1,3-oxazolidine -5,8'-1-azabicyclo[2.2.2]octane]-2-one, N-[(3R)-1-azabicyclo[2.2.2]oct-3-yl]-4-chlorobenzamide,5-morpholin-4-yl-pentanoic acid (4-pyridin-3-yl-phenyl)-amide, EVP-6124, EVP-4473, TC-6987, and MEM3454;
    wherein the composition is in a pharmaceutically acceptable form provided in a single dosage form.

2. The composition of claim 1, wherein the agonist is N-[(2S,3S)-2-(pyridin-3-ylmethyl)-1-azabicyclo [2.2.2]oct-3-yl]-1-benzofuran-2-carboxamide.

3. The composition of claim 1, wherein the nicotine is in the form of a free base, a salt, a complex, or a solvate.

4. The composition of claim 3, wherein the nicotine is nicotine polacrilex, nicotine free base, nicotine tartrate or nicotine bitartrate.

5. The composition of claim 1, wherein the composition is in a form adapted for oral ingestion.

6. The composition of claim 5, wherein the pharmaceutically acceptable form is selected from the group consisting of a pill, tablet, lozenge, mini lozenge, capsule, caplet, pouch, gum and spray.

7. The composition of claim 1, wherein the nicotine is nicotine polacrilex, nicotine free base, nicotine tartrate or nicotine bitartrate; and wherein the pharmaceutically acceptable form is a gum, lozenge, pouch or spray.

8. The composition of claim 1, wherein one or both of the nicotine and the agonist are sorbed onto a porous particulate carrier.

9. The composition of claim 8, wherein the porous particulate carrier comprises microcrystalline cellulose.

10. A method for treating a condition, disease or disorder responsive to stimulation of nicotinic acetylcholinergic receptors, comprising:
    orally or nasally administering an effective amount of a pharmaceutical composition to a human subject, the pharmaceutical composition comprising:
    nicotine; and
    an agonist or pharmaceutically acceptable salt thereof, having selectivity to an $\alpha_7$ nicotinic receptor subtype, wherein the agonist is selected form the group consisting of N-[(2S,3S)-2-(pyridin-3-ylmethyl)-1-azabicyclo [2.2.2]oct-3-yl]-1-benzofuran-2-carboxamide,(5aS,8S,10aR)-5a,6,9,10-Tetrahydro,7H,11H-8,10a-methanopyrido[2',3':5,6]pyrano[2,3-d]azepine, 1,4-Diazabicyclo[3.2.2]nonane-4-carboxylic acid,4-bromophenyl ester, 3-[(3E)-3-[(2,4-dimethoxyphenyl)methylidene]-5,6-dihydro-4H-pyridin-2-yl]pyridine, 2-methyl-5-(6-phenyl-pyridazin-3-yl)-octahydro-pyrrolo[3,4-c]pyrrole, (5S)-spiro[1,3-oxazolidine-5,8'-1-azabicyclo[2.2.2]octane]-2-one, N-[(3R)-1-azabicyclo

[2.2.2]oct-3-yl]-4-chlorobenzamide,5-morpholin-4-yl-pentanoic acid (4-pyridin-3-yl-phenyl)-amide, EVP-6124, EVP-4473, TC-6987, and MEM3454;

wherein the composition is in a pharmaceutically acceptable form provided in a single dosage form.

11. The method of claim 10, wherein said administering step comprises administering the pharmaceutical composition to a human subject as a smoking cessation aid.

12. The method of claim 10, wherein the agonist is N-[(2S,3S)-2-(pyridin-3-ylmethyl)-1-azabicyclo[2.2.2]oct-3-yl]-1-benzofuran-2-carboxamide.

13. The method of claim 10, wherein the nicotine is in the form of a free base, a salt, a complex, or a solvate.

14. The method of claim 10, wherein the nicotine is nicotine polacrilex, nicotine free base, nicotine tartrate, or nicotine bitartrate.

15. The method of claim 10, wherein one or both of the nicotine and the agonist are sorbed onto a porous particulate carrier.

16. The method of claim 15, wherein the porous particulate carrier comprises microcrystalline cellulose.

17. The method of claim 10, wherein the composition is in a form adapted for oral ingestion.

18. The method of claim 10, wherein the composition is in the form of a gum, lozenge, tablet, spray or a pouch product.

* * * * *